United States Patent [19]

Overgaard et al.

[11] Patent Number: 5,208,377
[45] Date of Patent: May 4, 1993

[54] PURIFICATION AND DECOLORIZATION OF OFF-COLOR ALKYL ALKANOLAMINES

[75] Inventors: Thomas H. Overgaard, Redford Township, Wayne County; Louis P. Verduce, Wyandotte, both of Mich.

[73] Assignee: Elf Atochem North America, Inc., Philadelphia, Pa.

[21] Appl. No.: 939,532

[22] Filed: Sep. 1, 1992

Related U.S. Application Data

[63] Continuation of Ser. No. 587,198, Sep. 24, 1990, abandoned.

[51] Int. Cl.$^5$ .......................................... C07C 213/00
[52] U.S. Cl. ................................................. 564/477
[58] Field of Search .................... 564/497, 499; 203/6, 203/31, 32

[56] References Cited

U.S. PATENT DOCUMENTS

| | | | |
|---|---|---|---|
| 3,207,790 | 9/1965 | Glew et al. | 260/584 |
| 3,453,183 | 7/1969 | Okubo et al. | 203/33 |
| 4,379,024 | 4/1983 | Gardner | 203/6 |

OTHER PUBLICATIONS

Antropov et al. "Effect of the Structure of Inhibitors, etc." *Chem. Abst.* vol. 76, No. 17 (1972) p. 208, Abst #102747k.

*Primary Examiner*—Richard L. Raymond
*Assistant Examiner*—Peter G. O'Sullivan

[57] ABSTRACT

Off-color N-(C$_4$-C$_{10}$)alkyl di(C$_2$-C$_3$) alkanolamines purified and decolorized by vacuum distillation at a pressure within the range of 1 to 50 mm.Hg (1-50 torr) in the presence of water and or water-soluble metal borohydride whereby the distilled alkanolamine has a reduced APHA color rating which is maintained on storage.

14 Claims, No Drawings

PURIFICATION AND DECOLORIZATION OF OFF-COLOR ALKYL ALKANOLAMINES

This is a continuation of copending application Ser. No. 07/587,198 filed on Sep. 24, 1990 now abandoned.

BACKGROUND OF THE INVENTION

This invention concerns the treatment of certain alkyl diethanolamines to inhibit color formation therein during manufacture or to remove color-forming contaminants therefrom after manufacture. More particularly, it concerns the purification and reduction in color of an off-color N-($C_4$–$C_{10}$) di($C_2$–$C_3$) alkanolamine by the addition of a color inhibiting amount of a water-soluble metal borohydride to said alkanolamine, and subjecting the product in the presence of water to vacuum distillation at a pressure of less than about 50 mm.Hg (millimeters of mercury).

There exist a significant demand for high purity/low color N-butyl diethanolamine in the photographic market. However, the product, as manufactured, contains impurities and is off-color. Vacuum distillation at about 100 mm.Hg will remove much of the impurities but high color rapidly returns on storage indicating the continued presence of color forming compounds.

THE PRIOR ART

U.S. Pat. No. 3,207,790 discloses the reduction of color of discolored alkanolamines by mixing into the off-color amine a quantity of a borohydride of an alkali metal. The process is said to be useful for a variety of alkanolamines including N,N-dibutyl ethanolamine and N-ethyl diethanolamine t reduce and stabilize color in these products. The disclosure does not suggest the subsequent removal of the borohydride or any other contaminants.

U.S. Pat. No. 4,379,024 discloses a manufacturing process for preparing alkylaminoalkanols wherein an alkali metal borohydride is added, to the crude alkylaminoalkanol before stripping excess reactant. Thereafter, the crude material with borohydride is subjected to a final distillation step at a reduced pressure in excess of 100 mm.Hg. to recover a pure, color-stable alkylaminoalkanol with the borohydride and impurities coming off as bottoms. The amine products shown to have been treated in the working examples of this patent are dimethyl and diethylaminoethanol.

STATEMENT OF THE INVENTION

This invention is a process for the preparation of high purity, low APHA color product from an N-($C_4$–$C_{10}$) alkyl di($C_2$–$C_3$) alkanolamine containing contaminants including color-forming bodies which comprises vacuum distilling said alkanolamine at a pressure of less than about 50 mm.Hg in the presence of water and a water-soluble metal borohydride whereby the distilled alkanolamine has a reduced APHA color rating which is maintained on storage.

DETAILED DESCRIPTION OF THE INVENTION

To provide a low APHA (American Public Health Association) color rating for N-butyl diethanolamine and higher homologs, it has not heretofore been known to sufficiently reduce the color-forming impurities in the crude product to provide a high purity material which is color-stable on storage. Previously, it was known to add an aqueous solution of an alkali metal borohydride to alkyl alkanolamines and vacuum distill at above 100 mm. Hg to provide a color-stable product (See U.S. Pat. No. 4,379,024). However, this procedure fails to produce color-stable N-butyl diethanolamine or higher alkyl homologs.

It has now been found that N-butyl diethanolamine and higher homologs may be color-stabilized and purified by the addition of an additive amount of a water-soluble metal borohydride to the dialkanolamine and vacuum distilling in the presence of water at a pressure of less than about 50, preferably from about 4 to about 10 mm.Hg, the distillate having a high purity and low APHA color on long term storage.

In the manufacture of N-butyl diethanolamine, one mole of N-butylamine is reacted with two moles of ethylene oxide in the presence of water (the catalyst). A minor excess of amine is maintained to assure complete reaction of the ethylene oxide. The crude reaction product may be subjected to multiple distillation steps to produce the pure product. The first distillation strips the residual water and excess butylamine. The second distillation removes N-butylaminoethanol. The next step isolates N-butyl diethanolamine product by vacuum distillation. The amount of N- butyl diethanolamine produced with the N-butyl aminoethanol co-product depends on the ratio of the amine to ethylene oxide reactants used.

The ethylene oxide reactant generally contains low part per million concentrations (approx, 10 ppm) of acetaldehyde. N-butylamine, depending on its source, may be contaminated with butyraldehyde (e.g., 50 ppm). Analysis of N-butyl diethanolamine that has been subjected to normal distillation temperatures (>175° C.) indicates the presence of additional aldehydes. It is believed that these aldehydes, present in the reactants and crude product, react with various components of the crude product to produce color bodies. The addition of the borohydride reduces the concentration of the aldehydes present in the crude product and the low pressure vacuum distillation less than about 50 mm.Hg permits the removal of the contaminants (including color-forming materials, color bodies and borohydride) at sufficiently low process temperature to avoid the reformation of addition 1 aldehydes and color bodies thereby providing color-stable and high purity N-butyl diethanolamine.

While the above discussion has been limited to the manufacture of N-butyl diethanolamines, it is also representative of those other alkanolamines included in the N-($C_4$–$C_{10}$) alkyl di($C_2$–$C_3$) alkanolamines which are a part of this invention. The alkyl groups included are, for example, butyl, isobutyl, pentyl, hexyl, isohexyl, 2-ethylhexyl, octyl, isoctyl, decyl and the like. The alkanol groups may be ethanol or isopropanol.

The process of this invention may include either a single low pressure vacuum distillation step or a multiple step or zone distillation, procedure including the low pressure vacuum distillation preferably used as the last distillation step. The additional distillation steps or zones may be operated at pressures above 50 mm.Hg so long as the low pressure vacuum distillation step is operated at less than about 50 mm.Hg, preferably between about 4 and about 10 mm.Hg. Since subjecting the high purity, low APHA color N-butyl diethanolamine and higher homologs of this invention to temperatures of 175° C. and higher will generate color-forming materials, i.e., aldehydes therein, the dialkanolamines should not be exposed to such temperatures either during vacuum distillation or thereafter.

Water concentration in the crude alkyl alkanolamine at the initial phase of distillation is preferably from 0.5 to 10% based o the weight of the crude material but may be higher. Preferably, an initial concentration of from about 1 to 3% is used. If multiple step distillation is employed, much of this water is removed overhead usually prior to the step or zone of reduction of pressure to the critical range. Water may be introduced as a part of the crude material or separately, as from the incorporation of the aqueous solution of water-soluble metal borohydride.

The water-soluble metal borohydride is preferably an alkali metal borohydride, particularly, sodium borohydride. However, other water-soluble metal salts, e.g., potassium, lithium, cesium and rubidium borhydrides will work in this process. The borohydride is generally introduced int the freshly manufactured crude alkanolamine product either at a point just prior to the removal of water and excess amine in the multi step distillation process, or to any off-color product prior to distillation. The amount of borohydride preferably ranges from about 0.05 to about 0.5 percent based on the weight of the crude alkanolamine product. The borohydride is preferably used in the form of an aqueous solution and may contain an alkali metal hydroxide as a stabilizer. The hydroxide is generally present in the aqueous solution in the amount of from 5 to 15%, preferably about 10% by weight of said solution.

The following examples are set forth to demonstrate the process of this invention. The use of N- butylamine and ethylene oxide is representative of other homologs which produce the N-($C_4$-$C_{10}$)alkyl di($C_2$-$C_3$) alkanolamines of this invention.

EXAMPLE 1

A slight excess of one molar proportion of N-butylamine and two molar proportions of ethylene oxide and 0.01 molar proportion of water (catalyst) were a charged to reactor and maintained at a temperature of 150° C. at autogenous pressure for about 5 minutes to complete the reaction. A small excess of N-butylamine was employed to assure complete reaction of the ethylene oxide. Crude aqueous product was withdrawn from the reactor and 0.12% of sodium borohydride, based on the weight of the crude product, was added. The sodium borohydride was in the form of an aqueous solution containing 10 weight % sodium hydroxide as a stabilizer. The water concentration of the crude product after addition of the aqueous borohydride solution was about 2 weight %.

The crude N-butyl diethanolamine product containing sodium borohydride was first distilled in a 25 mm., 10 plate column packed with nichrome helices where water and N-butylamine was removed overhead at a distillation pressure of 600 mm. Hg, an overhead temperature of 80° C. and a bottoms temperature of 145° C. The distillation bottoms was passed to a second column (25 mm., 10 plate tray and cap type) where coproduced N-butylaminoethanol was taken off overhead at a distillation pressure of 150 mm.Hg, an overhead temperature of 138° C. and a bottoms temperature of 172° C. The bottoms from the second distillation column was transferred to a third column which was a 25 mm. Oldershaw apparatus comprising a tray and cap type column. It contained 25 plates through the depth of the column. The reflux ratio (a comparison of the volume of condensed vapor returned to the top of the column and the volume of condensed vapor taken off as finished product) was maintained at about 5:1 during distillation. Pure N-butyl diethanolamine was removed overhead from this column operated at a pressure of 10 mm.Hg, an overhead temperature of 148° C. and a bottoms temperature of 188° C.

The pure N-butyl diethanolamine contained no low boilers, less than 0.1% water, a product assay [analysis by capillary gas chromatography (GC)] of 99.4% and an APHA color of 20 (APHA Color is determined by Platinum-Cobalt Color, Test Method D1209). The N-butyl diethanolamine product showed good color stability for over six months.

The specification requirements for N-butyl diethanolamine photographic material are (1) an APHA color rating of no greater than 50, (2) a water content of less than 0.1% and (3) an assay (GC) of 99%.

For comparative purposes, an off-color N-butyl diethanolamine having an assay of 99.16% with a water content of 0.22% and a non-determinable color rating due to the presence of a gray cast was charged to a 2 liter distillation unit in an amount of 1000 ml. The distillation unit consisted of a 2 liter flask, glascol heating mantle to heat the flask, thermometer well in the flask and a vacuum jacketed 25 plate Oldershaw column. Attached to the column was a distilling head adapter followed by a Friedrichs water condenser with a side arm. The side arm was connected in series to a straight bore stopcock and a 5 place vacuum manifold. The verticle sidearm of the distilling head adapter was connected to an Allihn condenser followed by a straight vacuum adapter and 500 ml. receiver (flask). The 5 place vacuum manifold was attached to a closed end manometer, dry ice trap, microvalve and both Allihn and Friedrichs condensers.

Distillation was conducted at 5 mm.Hg pressure, a 10:1 reflux ratio and no borohydride or other additive. The temperature of the distilland was 121° C. Of the seven distillation cuts made, only two passed all required specification parameters for photographic material, i.e., APHA color, assay and water content. These two cuts represent 17% of the total charge. The results for the seven cuts for this distillation run are as follows:

| Cut No. | % $H_2O$ | APHA Color | Assay | Receiving ml. |
| --- | --- | --- | --- | --- |
| 1 | 0.09 | 500+ | 94.44 | 62 |
| 2 | 0.15 | —* | 93.91 | 15 |
| 3 | 0.07 | 70 | 99.32 | 355 |
| 4 | 0.08 | 40 | 99.64 | 65 |
| 5 | 0.11 | 500+ | 98.28 | 53 |
| 6 | 0.08 | 40 | 99.60 | 105 |
| 7 | 0.06 | 100 | 99.62 | 220 |
| | | | | 875 |
| | | | Residue | 100 |
| | | | Total | 975 |

*The dash line indicates no results available.

Several other distillations were also run for comparative purposes. In one run 1000 ml. of off-color N-butyl diethanolamine was charged to a two liter flask connected to the equipment described above for the first comparative experiment. To this was added 10 ml. of sodium borohydride (12% aqueous solution). The distillation was conducted at 100 mm.Hg and the reflux ratio was maintained at 5:1. The temperature of the distillate was 222° C. The procedure resulted in no material acceptable for the photographic application.

In another comparative run using identical equipment as above, 1000 ml of off-color N-butyl diethanolamine was charged to a two liter flask with no additive addition. The distillation was conducted at 100 mm.Hg and the reflux ratio was maintained at 6:1. The temperature of the distillate was 224° C. The distillation resulted in no material acceptable for photographic application.

EXAMPLE 2

Using the distillation unit and off-color N-butyl diethanolamine of the experiment conducted for comparative purposes and reported in the foregoing example, two distillations were carried out to determine if excess water in the distillation procedure would improve the APHA color of the distillation cuts.

The first distillation consisted of 10 ml. of sodium borohydride (12 wt. % solution) and 50 ml. of water added to the 2 liter flask of the distillation unit containing 1000 ml. of the off-color N-butyl diethanolamine. The distillation was conducted at a pressure of 50 mm.Hg and the reflux ratio was maintained at approximately 6:1. The temperature of the distilland was 184° C. The results of analyses of cuts taken during this distillation are reported below.

The second distillation was conducted using the same procedure as described above for the first distillation except that the addition of 50 ml. of water was omitted and the reflux ratio was 5:1. The results of analyses of cuts taken during this distillation are reported below.

For comparative purposes, another distillation run was made as follows: 2200 ml of the off-color N-butyl diethanolamine described above was placed in a 3 liter flask which replaced the 2 liter flask of the above described distillation unit. In the absence of sodium borohydride or other additive, the distillation was carried out at an average pressure of 49 mm.Hg and a reflux ratio of 5:1.

Twelve cuts were taken during the above reported distillation runs and the cuts analyzed for APHA color and purity. The results of these analyses are reported below.

| Cut No. | % $H_2O$ | APHA Color | Assay | Receiver, ml. |
|---|---|---|---|---|
| First Distillation at 50 mm. Hg. (50 ml. $H_2O$) | | | | |
| 1 | 72.39 | 500+ | — | 76 |
| 2 | 0.28 | 50 | 98.84 | 140 |
| 3 | 36.30 | 500+ | — | 54 |
| 4 | 0.11 | 25 | 99.12 | 380 |
| 5 | 0.20 | — | 93.66 | 35 |
| 6 | 0.23 | 15 | 97.73 | 165 |
| | | | | 850 |
| | | | Residue | 190 |
| | | | Total | 1040 |
| Second Distillation at 50 mm. Hg (No $H_2O$ added) | | | | |
| 1 | 22.22 | — | 53.07 | 29 |
| 2 | 0.13 | 45 | 98.05 | 323 |
| 3 | 0.26 | — | 94.95 | 42 |
| 4 | 0.06 | 25 | 98.98 | 330 |
| 5 | 0.11 | 65 | 97.72 | 130 |
| | | | | 854 |
| | | | Residue | 125 |
| | | | Total | 979 |
| Comparative Distillation at 49 mm. Hg (No Additive) | | | | |
| 1 | 1.80 | 500+ | 90.23 | 110 |
| 2 | 0.48 | 500+ | 98.16 | 136 |
| 3 | 0.57 | ** | 98.66 | 172 |
| 4 | 0.14 | 65 | 99.77 | 338 |
| 5 | 1.66 | 500 | 96.79 | 64 |
| 6 | 0.12 | ** | 99.71 | 368 |
| 7 | 0.07 | ** | 99.74 | 198 |

| Cut No. | % $H_2O$ | APHA Color | Assay | Receiver, ml. |
|---|---|---|---|---|
| -continued | | | | |
| 8 | 2.07 | ** | 95.21 | 26 |
| 9 | 0.22 | ** | 99.27 | 100 |
| 10 | 0.10 | ** | 99.56 | 367 |
| 11 | 1.58 | — | 99.75 | 18 |
| 12 | 0.38 | 175 | 96.44 | 80 |
| | | | | 1977 |
| | | | Residue | 75 |
| | | | Total | 2052 |

** Unable to determine due to presence of gray cast background.

It has been determined experimentally that distillation alone, regardless of vacuum, will not recover appreciable quantities of acceptable N-butyl diethanolamine from off-color product. A combination of low distillation pressure and borohydride is necessary to produce the high purity, low APHA color required to meet the specifications of photographic use. The lower the pressure, below the prescribed upper limit, the higher the yield of acceptable product.

We claim:

1. A process for the preparation of high purity, low APHA color product from a crude N-($C_4$-$C_{10}$)alkyl di ($C_2$-$C_3$)alkanolamine containing contaminants including color-forming bodies which comprises vacuum distilling said alkanolamine at a pressure of less than about 50 mm. Hg in the presence of water and a water-soluble metal borohydride whereby the distilled alkanolamine has a reduced APHA color rating which is maintained on storage.

2. The process of claim 1 wherein said vacuum distillation is operated at a pressure of from 4 to 10 mm.Hg.

3. The process of claim 1 wherein said metal borohydride is an alkali metal borohydride.

4. The process of claim 3 wherein said alkali metal borohydride is present in an amount of from about 0.05 to about 0.5 percent based on the weight of said crude alkanolamine.

5. The process of claim 1 wherein the water present at the start of said distillation ranges from 0.5 to 10 percent based on the weight of said crude alkanolamine.

6. The process of claim 1 which includes multiple step distillation at least one of said steps operated at a pressure of less than 50 mm.Hg and in the presence of said water-soluble metal borohydride.

7. The process of claim 6 wherein the distillation step operated at a pressure of less than 50 mm.Hg is the last distillation step.

8. The process of claim 7 wherein the pressure of the last distillation step ranges from about 4 to about 10 mm.Hg.

9. The process of claim 6 wherein the metal borohydride is an alkali metal borohydride.

10. The process of claim 9 wherein said alkali metal borohydride is present in an amount of from about 0.05 to about 0.5 percent based on the weight of said crude alkanolamine.

11. The process of claim 1 wherein said N-($C_4$-$C_{10}$) alkyl di($C_2$-$C_3$)alkanolamine is N-butyl diethanolamine.

12. The process of claim 11 wherein said metal borohydride is an alkali metal borohydride and said pressure ranges from about 4 to about 10 mm.Hg.

13. The process of claim 12 which includes multiple step distillation and at least the last step of which is operated at a pressure ranging form about 4 to about 10 mm.Hg.

14. The process of claim 13 wherein the alkali metal borohydride is sodium borohydride and the water is present at the start of the vacuum distillation in an amount ranging from about 0.5 to about 10 percent based on the weight of the crude dialkanolamine.

* * * * *